(12) United States Patent  
Sandra et al.

(10) Patent No.: US 7,350,427 B2
(45) Date of Patent: Apr. 1, 2008

(54) SORBENT COLLECTOR MATERIAL BASED ON POLYORGANOSILOXANE

(75) Inventors: Patrick Sandra, Kortrijk-Marke (BE); Frank David, Bruegge (BE)

(73) Assignee: Gerstel Systemtechnik GmbH & Co., Muelheim (DE)

( * ) Notice: Subject to any disclaimer, the term of this patent is extended or adjusted under 35 U.S.C. 154(b) by 209 days.

(21) Appl. No.: 11/134,610

(22) Filed: May 20, 2005

(65) Prior Publication Data

US 2005/0288183 A1    Dec. 29, 2005

(30) Foreign Application Priority Data

May 27, 2004   (DE)   ................ 10 2004 026 485

(51) Int. Cl.
*G01N 1/22*   (2006.01)
(52) U.S. Cl. ............. 73/863.23; 73/31.02; 73/31.03; 73/864.82; 436/177
(58) Field of Classification Search ........... 73/23.35, 73/23.39, 23.4, 31.01–31.03, 61.52–61.55, 73/863, 863.11, 863.12, 863.21–863.23, 864.81–864.84; 436/177
See application file for complete search history.

(56) References Cited

U.S. PATENT DOCUMENTS

| | | | |
|---|---|---|---|
| 5,045,190 A | * | 9/1991 | Carbonell et al. ...... 210/198.2 |
| 5,965,803 A | * | 10/1999 | Chinn et al. ............ 73/23.34 |
| 6,134,945 A | * | 10/2000 | Gerstel et al. .......... 73/23.42 |
| 6,693,159 B1 | * | 2/2004 | Holmes et al. ......... 526/323.1 |
| 6,761,757 B2 | * | 7/2004 | Welker .................. 96/413 |
| 7,122,065 B2 | * | 10/2006 | Fox ....................... 55/306 |
| 2005/0014156 A1 | * | 1/2005 | Pawliszyn ................ 435/6 |

FOREIGN PATENT DOCUMENTS

| | | | |
|---|---|---|---|
| CH | 507 724 | | 12/1966 |
| DE | 197 26 164 A1 | | 12/1998 |
| GB | 1169523 A | * | 11/1969 |
| JP | 2002121472 | | 9/2003 |
| WO | WO 99/22861 A1 | | 5/1999 |
| WO | WO 00/46281 A2 | | 8/2000 |
| WO | WO 2004/037387 A2 | | 5/2004 |

OTHER PUBLICATIONS

Baltussen, Henricus, "New Concepts in Sorption Based Sample Preparation for Chromatography", Sep. 2000, pp. 1-241.*
Smith et al., "X-Ray Computed Tomography on a Cellular Polysiloxane under Compression", Journal of Cellular Plastics, May 2001, vol. 37, pp. 231-248.*

* cited by examiner

*Primary Examiner*—Hezron Williams
*Assistant Examiner*—David A. Rogers
(74) *Attorney, Agent, or Firm*—Townsend and Townsend and Crew LLP.; Henry Heines

(57) ABSTRACT

The invention relates to a sorbent collector material based on polyorganosiloxane for the microextraction of substances to be analysed, the collector material having an open-cell foam structure, and to a collector and a liner which include this collector material.

17 Claims, 2 Drawing Sheets

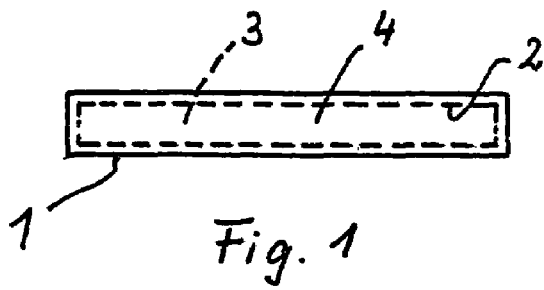
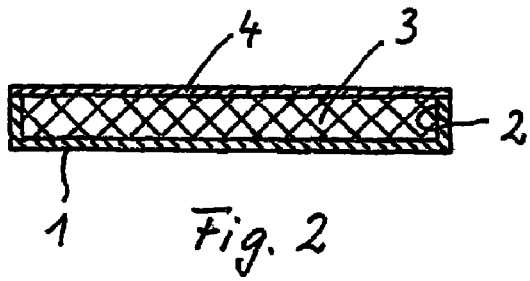
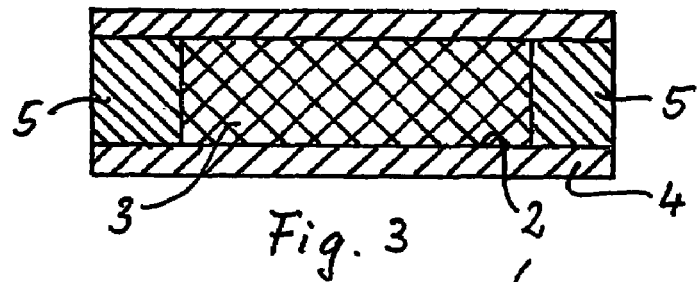
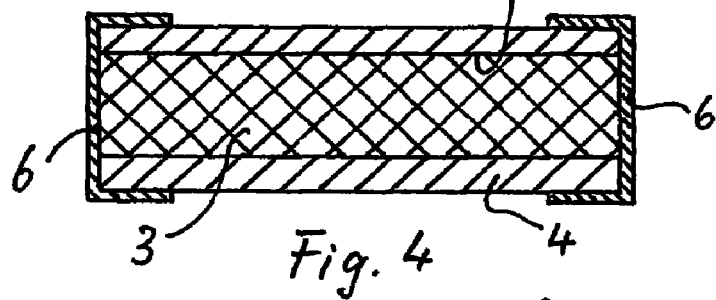
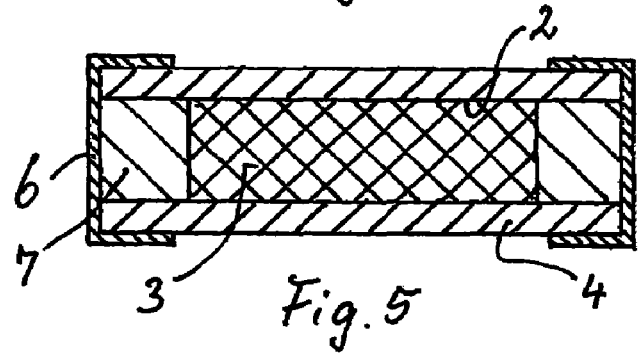

SORBENT COLLECTOR MATERIAL BASED ON POLYORGANOSILOXANE

FIELD OF THE INVENTION

The invention relates to a sorbent collector material based on polyorganosiloxane for the microextraction of substances to be analysed by microextraction in a chromatographic system.

BACKGROUND OF THE INVENTION

It is known in chromatography, in particular gas chromatography, to use collectors for the microextraction and subsequent analysis of substances to be analysed, for example in the form of exchangeable tubular sample vessels, known as liners, through which carrier gas can flow; these liners are provided with a layer or filling of a sorbent and/or adsorbent material for receiving the substances to be analysed. These may be collectors which take up and enrich the substances to be analysed externally from liquids and/or gases, in order for them then to be introduced into a chromatographic system, where the substances are desorbed (if appropriate by thermal means) and analyzed. However, the collectors may also be adsorption traps or cryotraps in the chromatographic system. Medium flows around or through the collectors for the purposes of desorption.

It is known to design collectors in the form of small tubes which have an internal coating of the sorbent and/or adsorbent material. However, this internal coating has a relatively low uptake capacity.

The latter is improved by providing a granular filling of the sorbent and/or adsorbent material. A filling of this type, if it allows absorption, as is the case with polyorganosiloxanes, offers a sufficiently large mass, or even a mass which is too large in relation to what is required. However, it is difficult to produce the filling material with a uniform particle size. In the collectors, this leads to different flow resistances for the passage of fluids, which are required at least during the desorption, and may even lead to blockages. The relatively high mass generally has an adverse effect on the chromatogram, on account of a strong background produced by corresponding "bleeding".

SUMMARY OF THE INVENTION

It is an object of the invention to provide a sorbent collector material for microextraction which has a sufficient fluid permeability while at the same time not having an excessively high mass.

This object is achieved by the sorbent collector material based on polyorganosiloxane being provided with an open-cell foam structure.

It is a further object of the invention to provide a sorbent collector for microextraction which comprises a sorbent collector material having a sufficient fluid permeability while at the same time not having an excessively high mass.

Thus, a further subject of the invention is a collector for the microextraction and analysis of substances to be analysed, comprising a layer which includes a first collector material of at least one material of the group consisting of a sorbent and adsorbent material, wherein a receiving space with a filling of a second collector material of at least one material of the group consisting of a sorbent and adsorbent material encapsulated therein is provided, the second collector material having a different selectivity from the first material, the layer being permeable to the substances which can be sorbed and adsorbed, respectively, by the second collector material, and the filling being at least partially covered with respect to the outside.

A further object of the invention is to provide a liner for microextraction which comprises a sorbent collector material having a sufficient fluid permeability while at the same time not having an excessively high mass.

Thus, an additional subject of the invention is a tubular liner for adding liquid samples to a chromatographic analysis system, wherein a plug of a collector material based on polyorganosiloxane being provided with an open-cell foam structure is arranged as a phase separation filter in the tube.

The foam structured collector material of the invention on the one hand offers a very large absorbent surface, which leads to rapid active mass transfer during passage of a fluid laden with substances to be analysed or of a carrier fluid, and also produces a pressure drop which is acceptable, i.e. not excessive, so that the absorption quality can be considerably improved compared to corresponding filler material in particle form, especially since a foam of this type can be produced in a very targeted way in terms of its structure and its relative density. Moreover, the equilibrium reaction of the foam material with individual substances, if it is not already known, can easily be determined. Moreover, a foam material of this type can be used in a very wide temperature range from approximately −70° C. to approximately +400° C., and on account of its relatively low mass makes only a small contribution to the chromatogram through "bleeding", i.e. the chromatogram of the foam material itself only has to be faded out to a small extent which, moreover, is calculable. The enrichment of substances to be analysed is more reproducible than with collector material in particle form. On account of the wide temperature use range, the collector material can be used in particular in chromatographic enrichment traps, and in particular also in cryotraps, but also in collectors for cold application systems and/or thermal desorption systems of chromatographs.

It is expedient for the porosity of the collector material to be such that, when a gas flows through in a quantity of 30 ml/min, which is customary in gas chromatography, the result is a pressure drop of <1 bar, in particular <0.8 bar.

The collector material can easily be converted into any form and is expediently soft, so that it can readily be introduced into a casing, for example in the form of a small tube or a flexible hose, and gas or liquid can then flow through it freely on account of the open-cell structure. The collector material preferably has a relative density of approximately 0.15 to 0.25 g/cm$^3$, and generally also a low water absorption capacity of <5%.

The collector material may be filled with a filler material, for example a pigment, and may furthermore be doped with at least one component which chemically reacts with substances to be analysed, during which process reaction products are sorbed or adsorbed, if only the reaction products but not their starting substances can be detected by chromatography. One example of this application is the extraction of aldehydes and ketones on a material impregnated with penta fluoro benzyl hydroxyl amine, in which case the carbonyl functions of the compounds which are of interest form a typical volatile reaction product which can be sorbed, thermally desorbed and analyzed by chromatography. Other examples include the derivatization of phenols and amines by acylation, the derivatization of thiols and the reaction of ethylene oxide with hydrogen bromide. For example, the covering layer may be of multi-layer structure, in which case an individual layer contains at least one chemically reacting component.

Poly dimethyl siloxane in open-cell foam form is particularly suitable as collector material.

A collector, for example in the form of a liner, may in particular also have a receiving space with a filling of the open-cell collector material encapsulated therein, this filling being at least partially covered with respect to the outside by a layer, the filling and the layer consisting of different sorbent and/or adsorbent materials, and therefore having different selectivity with respect to substances to be analysed, the layer being permeable to the substances which can be sorbed and/or adsorbed by the open-cell collector material of the filling. This on the one hand results in an increased uptake spectrum for substances to be analysed and on the other hand allows quantitative analysis over the entire uptake spectrum, since the open-cell collector material is not in contact with the outside space, and therefore also does not release any substances which have been taken up back into the outside space. Rather, these substances can be desorbed in a chromatograph, for example by thermal desorption, together with the substances taken up by the material of the covering layer, so that virtually undisturbed quantitative analysis is made possible. The encapsulation ensures an airtight closure, so that substances which have been taken up by the open-cell collector material cannot be released again to the outside.

In particular, the covering layer is hydrophobic and/or lipophobic, so that the filling, on account of the encapsulation, does not come into contact with water or oil or fats.

The covering layer may also be designed to act as a selective, semi-permeable membrane. Moreover, the covering layer may also be formed from different, sorbent and/or adsorbent materials arranged mixed with one another or in a plurality of layers.

Examples of suitable materials for the covering layer include polyethylene glycol, octadecyl trichloro silane, polymethyl vinyl chloro silane, polyacrylate, LDPE (low density polyethylene) or polyimide.

The different selectivity of the materials for the filling and the covering layer may relate to the volatility and/or the polarity of the substances to be analysed. These materials are to be selected accordingly.

Further objects, advantages and embodiments of the invention may be gathered from the following description.

BRIEF DESCRIPTION OF THE DRAWINGS

The invention is explained in more detail below in combination with exemplary embodiments illustrated in the appended drawings.

FIGS. 1 and 2 show a plan view and a sectional view of an embodiment of a collector of the invention.

FIGS. 3 to 5 show further embodiments of collectors of the invention.

DETAILED DESCRIPTION OF PREFERRED EMBODIMENTS

Figures 6, 7, 8:
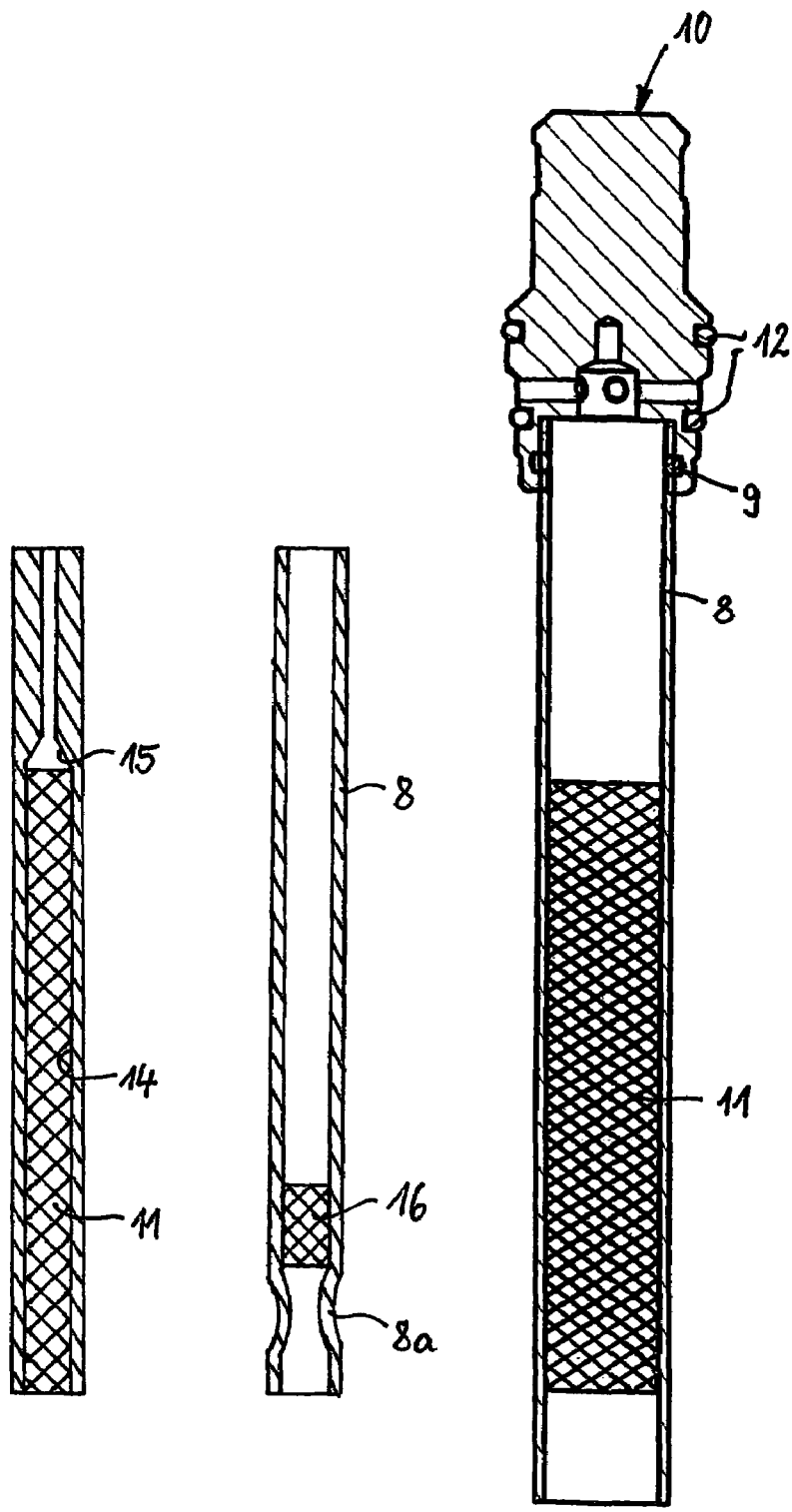
FIGS. 6 to 8 show a sectional view through three embodiments of a liner of the invention.

In the embodiment of a collector illustrated in FIGS. 1 and 2, the collector comprises a trough-like vessel 1, for example made from glass, metal or plastic material, which has a receiving space 2 filled with a filling 3 which is encapsulated in the vessel 1 by a layer 4 which covers its receiving space 2 with respect to the outside and closes it off tightly. The layer 4 consists of a first sorbent and/or adsorbent material, and the filling 3 consists of a second sorbent and/or adsorbent collector material based on polyorganosiloxane with an open-cell foam structure and a different selectivity from the first material.

Although the vessel 1 illustrated is substantially in the form of a rod, it may also take other forms, for example it may be round when seen from above. The cross section taken perpendicular to the plane of FIG. 2 may likewise differ, for example may be rectangular, semicircular, partially oval or the like.

Furthermore, in the reverse arrangement, it is also possible for a plate to be formed from a carrier material instead of the layer 4 and for the part which forms the vessel 1 in the embodiment shown in FIGS. 1 and 2 to be made from the first material, and therefore to form the layer 4 which covers the filling 3 over a relatively large area. The plate may consist of magnetic or magnetizable material, so that the collector can be used as a magnetic stirrer or can be attached to a magnetic holder for collection purposes. For this purpose, however, it is also possible for a magnet, for example a bar magnet, to be inserted into the receiving space 2 in addition to the filling or to be adhesively bonded to the outside of the collector.

In the embodiments illustrated in FIGS. 3 to 5, the layer 4 forms a flexible tube, the interior of which forms the receiving space 2 for the filling 3.

In FIG. 3, the flexible tube is tightly closed at each of its ends by a stopper 5. The stoppers 5 are, for example adhesively bonded in place. The stoppers 5 may consist of the same material as the flexible tube or of a different material, such as glass, metal or plastic. If stoppers 5 made from magnetic or magnetizable material are used, the collector can be used as a magnetic stirrer or can be attached to a magnetic holder.

In FIG. 4, the flexible tube is tightly closed at each of its ends by a cap 6. The caps 6 may consist of the same material as the flexible tube or of a different material, such as glass, metal or plastic. If caps 6 made from magnetic or magnetizable material are used, the collector can be used as a magnetic stirrer or can be attached to a magnetic holder.

In the embodiment illustrated in FIG. 5, inserts 7 of magnetic or magnetizable material are additionally fitted into the flexible tube at the ends, adjacent to the caps 6, in order to allow the collector to be used as a magnetic stirrer or to be attached to a magnetic holder. If stoppers 5 are used to close off the flexible tube, it is also possible for inserts 7 to be arranged in the latter, preferably adjacent to the stoppers 5.

The embodiment of a liner illustrated in FIG. 6 comprises a tube 8, which may consist of glass, metal or plastic material and is held by means of an O-ring 9 of a conveyor head 10. In the tube 8 there is a packing 11 of open-cell polyorganosiloxane foam. The conveyor head has seals 12, by means of which it can be fitted in a sealing manner into a feeder device of a gas chromatograph, in which cases bores 13 for supply of a carrier gas to the interior of the liner open out between the seals 12.

If appropriate, the liner may have holding means (not shown) which hold the packing 11 in place in the tube 8 against the force exerted on the packing 11 by the carrier gas flowing through. These holding means may, for example, be a notch, i.e. a narrowed section 8a at the outlet end of the tube 8, or a glass frit or the like fitted at the outlet end of the tube 8. However, the packing 11 may also be held by the clamping force of the foam, which is compressed slightly when it is introduced into the tube 8, without the need to provide an additional holding means.

In the embodiment illustrated in FIG. 7, the externally cylindrical liner is provided with a continuous bore 14, which is stepped as a result of the formation of a shoulder 15, with the packing 11 being accommodated in the region of the bore 14 with the larger diameter.

The packing 11 may also be formed in such a way that it also fills the space delimited by the shoulder 15. This has the advantage that water can be drawn through, for example by pumping, in the direction towards the shoulder 15, i.e. towards the region of the bore 14 with a smaller diameter, without there being any dead space in which the formation of droplets can occur all the way to the shoulder 15. The packing can then be dried at low temperature, after which first of all heating is carried out in order to desorb the substances to be analysed, with carrier gas being passed through in the opposite direction.

Of course, holding means for retaining the packing 11 may also be provided in the embodiment shown in FIG. 7.

Furthermore, in certain applications, in which liquid specimens to be added contain solid particles, it is expedient for the specimens to be added, for example by means of a syringe, via a liner which, as illustrated in FIG. 8, contains a plug 16 of polyorganosiloxane foam which, although permeable to the specimen liquid, retains solid particles. The plug 16 then serves as a phase separation filter. This has the advantage over filtering of the specimens before the specimen is added to the analysis system that substances which are contained in the specimen and would be removed during filtering, even though they are at least partially also retained by the plug 16, can be desorbed again at a later stage at a gentle temperature and are therefore likewise available for analysis. If appropriate, given a suitable mass of the plug 16 of polyorganosiloxane foam, it is also possible to deliberately enrich certain substances from the specimen. Therefore, in these applications the plug 16 represents a highly inert filter, since the analysis results are scarcely distorted by it at all.

The collector material according to the invention is also suitable to be injected with liquid water, for example via a syringe or pump, in order to take up and enrich organic substances therefrom for the purpose of later analysis without being significantly deactivated.

Moreover, the collector material can be used for a VOC (volatile organic compound) trap, for example between two chromatography columns.

While the invention has been shown and described with reference to preferred embodiments, it should be apparent to one of ordinary skill in the art that many changes and modifications may be made without departing from the spirit and scope of the invention as defined in the claims.

What is claimed is:

1. A collector for the microextraction and analysis of substances to be analysed, comprising a layer which includes a first collector material of at least one material of the group consisting of a sorbent and adsorbent material, the interior of which forms a receiving space with a filling of a second collector material of at least one material of the group consisting of a sorbent and adsorbent material encapsulated therein is provided, the second collector material having a different selectivity from the first material, the layer being permeable to the substances which can be sorbed and adsorbed, respectively, by the second collector material, and the filling being at least partially covered with respect to the outside by the first collector material wherein the filling has a higher selectivity with respect to highly volatile components of the substances to be analysed than the covering layer.

2. The collector according to claim 1, wherein the layer is of at least one material of the group consisting of a hydrophobic and lipophilic material.

3. The collector according to claim 1, wherein the materials of the layer and of the filling have different polarities.

4. The collector according to claim 1, wherein the ratio of the mass of the first and second materials used for the filing and the layer is matched to the particular application.

5. The collector according to claim 1, wherein at least one of the layer and the filling contains at least one component which chemically reacts with substances to be analysed.

6. The collector according to claim 1, wherein it is designed as a rod.

7. The collector according to claim 6, wherein the layer forms a flexible tube which accommodates the filling and is tightly closed at the ends.

8. The collector according to claim 7, wherein the flexible tube is closed by closures in the shape of a cap or a stopper.

9. The collector according to claim 6, wherein it is a magnetic stirrer.

10. The collector according to claim 9, wherein the rod at its ends is provided with a material of the group consisting of magnetic and magnetizable materials.

11. The collector according to claim 10, wherein the rod, as a flexible tube provided with the filling, is provided at its ends with end pieces out of the group consisting of caps and stoppers and inserts, made from magnetic or magnetizable material.

12. The collector according to claim 1, wherein the layer is formed using a material selected from the group consisting of polyethylene glycol, octadecyl trichlorosilane, polymethyl vinylchlorosilane, LDPE (low density polyethylene) and polyimide as first collector material.

13. The collector according to claim 1, wherein the layer forms a membrane that is selective with respect to the substances to be analysed.

14. The collector according to claim 1, wherein it is designed as a tubular, gas-permeable liner containing a packing of the collector material.

15. The collector according to claim 14, wherein the packing is arranged in a larger-diameter region of a stepped bore.

16. The collector according to claim 15, wherein the stepped bore has a conical transition region, formed by a shoulder, between the regions of different diameter.

17. The collector according to claim 16, wherein the transition region is also filled by the packing.

* * * * *